United States Patent [19]

Wolf

[11] 4,124,373
[45] * Nov. 7, 1978

[54] TETRAHYDROINDAZOLE HERBICIDES

[75] Inventor: Anthony D. Wolf, Newark, Del.

[73] Assignee: E. I. Du Pont de Nemours and Company, Wilmington, Del.

[*] Notice: The portion of the term of this patent subsequent to Nov. 22, 1994, has been disclaimed.

[21] Appl. No.: 756,439

[22] Filed: Jan. 3, 1977

[51] Int. Cl.$^2$ .................. A01N 9/22; C07D 231/56
[52] U.S. Cl. ......................... 71/92; 548/369; 548/359
[58] Field of Search ............. 260/310 R; 71/92; 548/369, 371, 372

[56] References Cited

U.S. PATENT DOCUMENTS

| 3,364,227 | 1/1968 | Robinson | 260/310 R |
| 3,637,738 | 1/1972 | Gschwend | 260/310 R |
| 4,059,434 | 11/1977 | Wolf | 71/92 |

OTHER PUBLICATIONS

Jacquier et al., Chem. Abst., vol. 67, 1967, 43768g.
Farbenfabriken, Chem. Abst., vol. 60, 6957.
Nunn et al., Chem. Abst., vol. 82, 170804a.

Primary Examiner—Natalie Trousof
Assistant Examiner—Jane T. Fan

[57] ABSTRACT

Herbicidal tetrahydroindazoles of the formula:

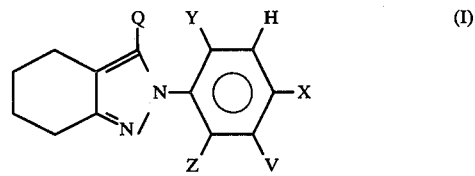

where
Q is chlorine, bromine or methyl;
X is hydrogen, methyl, chlorine, methoxy, ethoxy, or bromine;
Y is hydrogen, methyl, chlorine or methoxy;
V is hydrogen, methyl or chlorine; and
Z is hydrogen or methyl; with the proviso that
 (a) when Y and Z are methyl, X must be hydrogen, methyl, chlorine, or bromine;
 (b) when Y is hydrogen or chlorine and V is hydrogen or chlorine and Z is hydrogen, X must be hydrogen, methyl, or ethoxy; and
 (c) at least one of X, Y, V or Z must be hydrogen.

26 Claims, No Drawings

TETRAHYDROINDAZOLE HERBICIDES

BACKGROUND OF THE INVENTION

Recently, in German Offenlegungsschrift No. 2,165,651 a group of isoindole-1,3-diones which are useful as herbicides was disclosed. The general formula for the isoindole-1,3-diones disclosed in the Offenlegungsschrift is as follows:

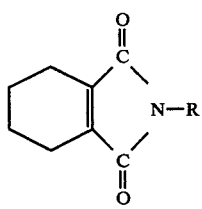

wherein R may be an aryl, aralkyl or benzyl substituent optionally substituted with 1 to 5 halogen atoms or a hydroxy, nitro, cyano, thiocyanato, carboxy, alkyl or halogenated alkyl, alkoxy, lower alkylthio or phenyl group. R may also be optionally substituted with a group having the configuration —O—CH$_2$A, where A is a phenyl or a naphthyl group. The phenyl group may be substituted with one or more halogen atoms, nitro groups, lower alkyl groups, or lower alkoxy groups.

Typical of the compounds disclosed in the Offenlegungschrift is the compound of Structure 1:

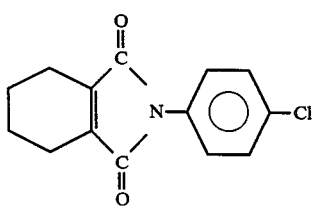

Although th compounds disclosed within the Offenlegungschrift are active herbicides, the need still exists for even etter herbicides. Weeds are very damaging to important crops such as rice and wheat and they decrease crop yield. In the current world situation, wherein food shortages are acute, it is most important to harvest the maximum possible yields of crops such as rice or wheat. Thus, a need exists for a particularly effective herbicide which will destroy as many weeds as possible without causing significant damage to desired crops, e.g., rice and wheat.

According to the instant invention, compounds have been discovered which are highly active herbicides and yet cause minimal damage to certain desired crops, e.g., rice and wheat and especially the major world food crop, rice.

The preparation and fungicidal utility of 2-(4-chlorophenyl)-1,2,4,5,6,7-hexahydro-3H-indazol-3-one is disclosed in Takeda Chem. Ind. Paper, Chem. Abs., 67, 11542h (1967).

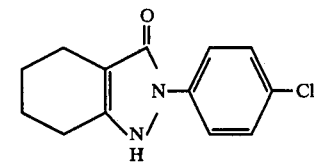

2-Aryl-4,5,6,7-tetrahydro-1-alkyl-1-H-indazol-3(2H)ones are claimed as antipyretics in Ger. Pat. No. 668.628 [assigned to P. Beierdorf & Co. AG, Chem. Abs., 33, 5131$^2$ (1939)]and U.S. Pat. No. 2,104,348 [asigned to E. R. Squibb Co., Chem. Abs., 32, 1869$^1$ (1938).]

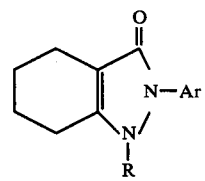

1-Phenyl-3,4-trimethylenepyrazolone is disclosed in U.S. Pat. No. 1,685,407 (1928) with utility as intermediate for making dyes and medicinal compounds. C. Mannich in Arch. Pharm. 267, 699–702 (1929) and in Brit. Pat. No. 260,577 describes the preparation of 1-phenyl-3,4-trimethylenepyrazolones.

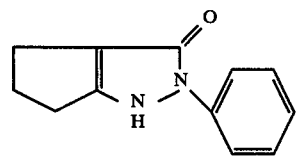

R. P. Williams et al. in J. Med. Chem. 13, 773 (1970) reports the preparation and evaluation as anti-inflammatory agents compounds of the following type:

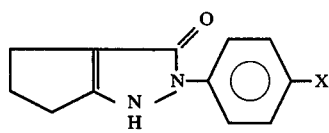

X = H, Br, F.

DESCRIPTION OF THE INVENTION

This invention relates to the novel compounds of Formula I to agricultural compositions containing them, and to the method of use of these compounds as general or selective herbicides having both pre- and post-emergence activity.

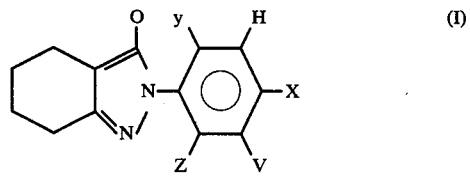

where

Q is chlorine, bromine or methyl;

X is hydrogen, methyl, chlorine, methoxy, ethoxy, or bromine;

Y is hydrogen, methyl, chlorine or methoxy;

V is hydrogen, methyl or chlorine; and

Z is hydrogen or methyl; with the proviso that (a) when Y and Z are methyl, X must be hydrogen, methyl, chlorine, or bromine;

(b) when Y is hydrogen or chlorine and V is hydrogen or chlorine and Z is hydrogen, X must be hydrogen, methyl or ethoxy; and (c) at least one of X, Y, V or Z must be hydrogen.

Of those compounds of Formula I, preferred for their high herbicidal activity or favorable cost or both are those compounds where, independently (1) X, Y, Z or V are hydrogen or methyl; or (2) Q is chlorine or methyl.

More preferred for their higher herbicidal activity or more favorable cost or both are those compounds of Formula I where X, Y, V or Z are hydrogen or methyl and Q is chlorine or methyl.

Specifically preferred for their outstanding herbicidal activity or highly favorable cost or both are:

(1) 3-chloro-2-(phenyl)-4,5,6,7-tetrahydro-2H-indazole.

(2) 2-(phenyl)-3-methyl-4,5,6,7-tetrahydro-2H-indazole.

SYNTHESIS OF THE COMPOUNDS

The novel tetrahydroindazole herbicides of Formula I where Q is chlorine or bromine (i.e., Ia, Ib, respectively), may be prepared in two steps as shown by equations A and B.

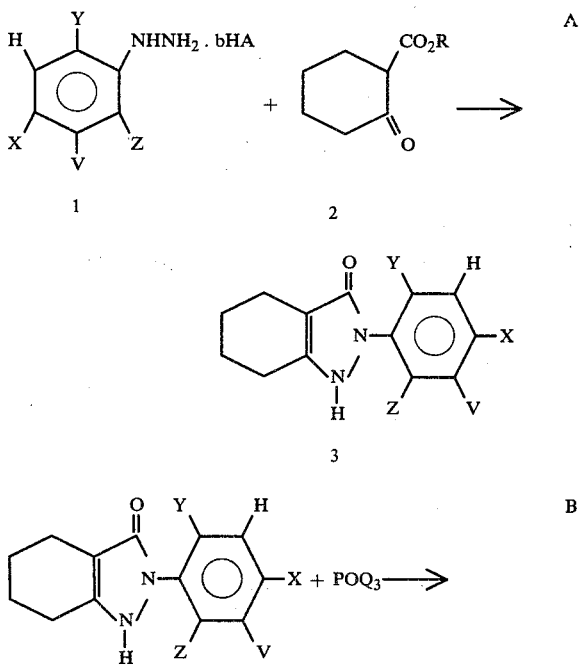

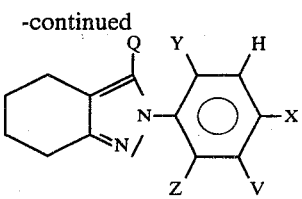

(I)
Ia: Q = Cl
Ib: Q = Br

Those compounds of Formula I in which Q is methyl are prepared in one step as shown by equation C.

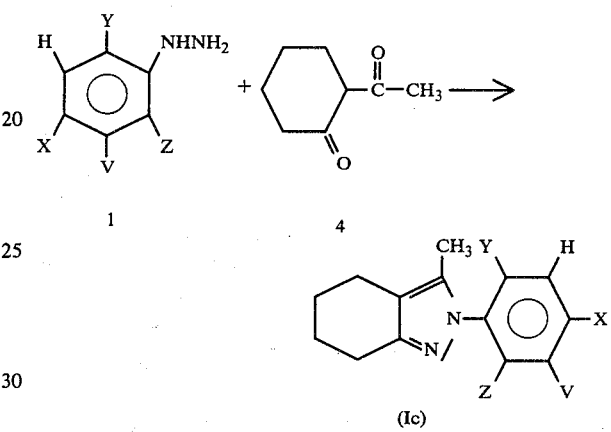

Where

Q, X, Y, V and Z are as defined above;

R is alkyl of 1–3 carbon atoms;

b is 0 or 1; and

A is anion of the corresponding acid HA having an ionization constant of at least $1 \times 10^{-7}$, e.g. $H_2SO_4$ or HCl.

The preparation of the tetrahydroindazolones 3 is known in the literature; for example, the preparation of 2-aryl-1,2,4,5,6,7-hexahydro-3H-indazol-3-one is described in W. Dieckmann, *Ann.*, 317, 102 (1901). The β-keto ester 2 is combined with the appropriate arylhydrazine acid salt 1 in an appropriate solvent, such as lower alcohols or aromatic hydrocarbons, and, optionally, in the presence of an acid acceptor, such as a tertiary organic amine or alkali metal hydroxide or alkoxide. The reaction mixture is heated at reflux for 0.5–24 hours. The tetrahydroindazolones 3 are isolated by conventional techniques such as by pouring the reaction mass into water and filtering the product. The crude product is usually of sufficient purity to be used directly in the next step. If necessary, futher purification can be accomplished by recrystallization, sublimation, or other conventional techniques known to those skilled in the art.

The novel tetrahydroindazoles of Formula Ia are obtained by heating the tetrahydroindazolones 3 with phosphouous oxychloride. When Q is bromine, the Formula I phosphorous oxybromide in the presence of an N,N-dialkylaniline and dimethylformamide is used (Equation B).

The use of an inert organic solvent such as methylene chloride or toluene is optional; however, it is preferred that no solvent other than the phosphorous oxyhalide be used. The mixture is heated at 100°–180° C., preferably 140°-150° C., for a period of 1-10 hours. The crude reaction mixture is dissolved in an inert organic solvent (e.g., CHCl$_3$, CH$_2$Cl$_2$, or toluene), and the solution is washed with dilute aqueous base (e.g., NaOH or KOH) followed with water. The organic phase is dried, and the solvent is removed on a rotary evaporator or by distillation. The product obtained is the tetrahydroindazole of Formula I which may be purified by distillation, sublimation or crystallization from an appropriate solvent.

The tetrahydroindazoles of Formula Ic are prepared by combining the 2-acetylcyclohexanone (4) with an arylhydrazine (1) in an appropriate solvent, such as an aromatic hydrocarbon, i.e. xylene, toluene, or chlorobenzene, followed by azeotropic removal of the water formed by the reaction. An acid catalyst, i.e., acetic acid, p-toluenesulfonic acid, etc., facilitates the reaction. Generally the progress of the condensation can be followed by measuring the volume of water removed from the reaction. At reflux temperature, 0.5-24 hours are required. A solvent such as a high boiling alcohol e.g., ethylene glycol may also be used in which case it is not necessary to remove water from the reaction. A by-product in this preparation often times is the isomeric 1H-tetrahydroindazole. The desired tetrahydroindazoles Ic are isolated by solvent removal and crystallization of the resultant solid or oil from a hydrocarbon solvent, i.e. hexane, heptane, by distillation or by chromotography of the crude product.

The intermediate β-keto esters 2 as well as 2-acetylcyclohexanone 4 are commercially available. They can also be prepared by methods described in the literature, see for example G. Stork et al. *J. Am. Chem. Soc.*, 85 207 (1963).

Many of the arylhydrazines (1) employed in this invention are also commercially available materials. Additionally, they can be prepared by methods known in the literature, see for example G. H. Colemen, *Organic Synthesis, Coll. Vol. I*, J. Wiley & Sons, New York, p. 442, which describes the preparation of phenylhydrazine. The general procedure is illustrated in equation D.

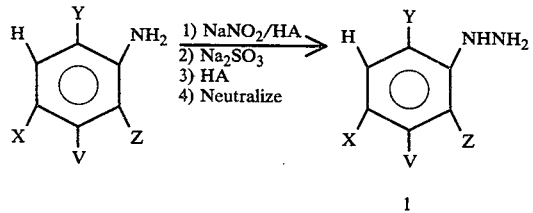

1

A = acid of ionization constant of at least 1 × 10$^{-7}$ e.g. H$_2$SO$_4$ or HCl The following examples further illustrate the method for synthesis of compounds of this invention. All parts are by weight and all temperatures are in degrees centigrade.

EXAMPLE 1

Preparation of
2-phenyl-1,2,4,5,6,7-hexahydro-3H-indazole-3-one 32.9 Parts of a mixture containing 60% 2-carboethoxycyclohexanone and 40% of 2-carbomethoxycyclohexanone purchased from Aldrich Chemical Company, Milwaukee, Wisconsin 53233, and 21.6 parts of phenylhydrazine purchased from Eastman Organic Chemicals Company, Rochester, N.Y. 14650, were admixed in 200 parts of toluene containing 2.0 parts of acetic acid. The mixture was refluxed for two hours with water removal. The resulting yellow suspension was cooled to 0°. The solid was collected, washed with hexane and dried. The yield was 37.1 parts of white solid with m.p. 178°-181°.

EXAMPLE 2

Preparation of
3-chloro-2-phenyl-4,5,6,7-tetrahydro-2H-indazole.

2.0 Parts of 2-phenyl-1,2,4,5,6,7-hexahydro-3H-indazole-3-one and 2.15 parts of phosphorous oxychloride were mixed and heated to 140° for 6 hours. The resulting crude product was taken up in about 100 parts of chloroform. The chloroform solution was extracted three times with 25 parts of 10% sodium hydroxide solution followed by an extraction with 25 parts of water. The chloroform solution was dried over anhydrous sodium sulfate and filtered. The solvent was removed on a rotary evaporator at a reduced pressure of 100-300 mm, and 1.6 parts of product were obtained as an oil. Further purification can be achieved by distillation at 130°-140° at .15 to .20 mm.

By using the procedure of Example 2 with the appropriate 2-aryl-1,2,4,5,6,7-hexahydro-3H-indazole-3-one and phosphorous oxychloride, the following compounds of Formula Ia may be prepared:

| X | Y | V | Z | m.p. |
|---|---|---|---|---|
| H | CH$_3$ | H | CH$_3$ | |
| H | Cl | Cl | H | i.r. bands: 1560, 818cm$^{-1}$ |
| CH$_3$ | H | Cl | H | $n_D^{25}$ = 1.6013 |
| CH$_3$ | Cl | Cl | H | |
| CH$_3$O | H | H | H | |
| Cl | CH$_3$O | H | H | 75-78° |
| H | H | Cl | H | b.p. 140-142° at .25mm |
| CH$_3$ | H | Cl | H | i.r.bands: 1580, 1570, 870, 822cm$^{-1}$ |
| Cl | CH$_3$ | H | H | i.r.bands: 1620, 1580, 825cm$^{-1}$ |
| H | H | CH$_3$ | H | $n_D^{25}$ = 1.5893 |
| Br | H | CH$_3$ | H | $n_D^{25}$ = 1.6120 |
| H | CH$_3$ | H | H | $n_D^{25}$ = 1.5780 |
| CH$_3$ | CH$_3$ | H | CH$_3$ | |
| Cl | CH$_3$ | H | CH$_3$ | |
| H | CH$_3$ | CH$_3$ | CH$_3$ | |
| H | CH$_3$ | Cl | CH$_3$ | |
| H | CH$_3$O | CH$_3$ | H | $n_D^{25}$ = 1.5702 |
| CH$_3$CH$_2$O | H | H | H | |

EXAMPLE 3

Preparation of
3-bromo-2-phenyl-4,5,6,7-tetrahydro-2H-indazole.

37.1 Parts of 2-phenyl-1,2,4,5,6,7-hexahydro-3H-indazole-3-one and 54.7 parts of phosphorous oxybromide purchased from Alpha Inorganics, Inc., Beverly, Mass., were mixed in 300 parts of xylene containing 28.4 parts of N,N-diethylaniline. The yellow reaction mixture was refluxed for about 16 hours and then cooled to room temperature. The xylene was decanted. 200 Parts of methylene chloride was added to the xylene and the organic solution of the product was washed with a solution of 5% sodium bicarbonate followed by washing with saturated salt solution. The solution was dried over anhydrous sodium sulfate. The solution of the product was filtered. The solvent was removed by evaporation on a rotary evaporator at reduced pressures (100-300 mm). The yellow oil obtained solidified. Recrystallization of the crude solid from hexane at 0°C gave 15.3 parts of a solid with m.p. 59°-62°. Further cooling to −78° gave an additional 9.0 parts of product with m.p. 49°-55° C.

By using the procedure of Example 3 with the appropriate 2-aryl-1,2,4,5,6,7-hexahydro-3H-indazole-3-one and phosphorous oxybromide, the following compounds of Formula Ib may be prepared:

| X | Y | V | Z |
|---|---|---|---|
| H | $CH_3$ | H | $CH_3$ |
| $CH_3$ | H | H | H |
| $CH_3$ | Cl | H | H |
| $CH_3O$ | Cl | Cl | H |
| H | H | Cl | H |
| $CH_3$ | H | Cl | H |
| Cl | $CH_3$ | H | H |
| $CH_3$ | H | $CH_3$ | H |
| Cl | $CH_3O$ | H | H |
| $CH_3$ | $CH_3$ | H | $CH_3$ |
| Cl | $CH_3$ | H | $CH_3$ |
| H | $CH_3$ | $CH_3$ | $CH_3$ |
| H | $CH_3$ | Cl | $CH_3$ |
| Br | H | $CH_3$ | H |
| $CH_3CH_2O$ | H | H | H |

EXAMPLE 4

Preparation of 3-methyl-2-phenyl-4,5,6,7-tetrahydro-2H-indazole.

2.2 Parts of phenylhydrazine and 2.8 parts of 2-acetylcyclohexanone purchased from Aldrich Chemical Co., Milwaukee, Wis. 53233, was mixed with 0.005 parts of p-toluenesulfonic acid in 50 parts ethylene glycol. The mixture was heated for one hour at 160° and then for an additional 16 hours at 100°. The resulting product was cooled and then poured into 300 parts of water. The crude oil which separated was extracted from the aqueous solution with 300 parts of ether. The ether layer was dried with anhydrous sodium sulfate and then filtered. The solvent was removed at reduced pressure (100-300mm) on a rotary evaporator. 3.2 Parts of an oil containing the product were obtained (i.r. bands for the oil at 1600, 760cm$^{-1}$).

By using the procedure of Example 4 with the appropriate arylhydrazine and 2-acetylcyclohexanone, the following compounds may be prepared:

| X | Y | V | Z | Physical Properties |
|---|---|---|---|---|
| $CH_3$ | H | H | H | i.r. bands 1630, 1610, 825cm$^{-1}$ |
| H | H | H | $CH_3$ | |
| $CH_3$ | Cl | Cl | H | |
| $CH_3O$ | Cl | Cl | H | |
| $CH_3$ | H | Cl | H | |
| Cl | $CH_3$ | H | H | |
| $CH_3$ | H | $CH_3$ | H | |
| Cl | $CH_3O$ | H | H | |
| $CH_3$ | $CH_3$ | H | $CH_3$ | |
| Cl | $CH_3$ | H | $CH_3$ | |
| H | $CH_3$ | $CH_3$ | $CH_3$ | |
| H | $CH_3$ | Cl | $CH_3$ | |
| Br | H | $CH_3$ | H | |
| $CH_3CH_2O$ | H | H | H | |

Formulations

Useful formulations of the compounds of Formula I can be prepared in conventional ways. They include dusts, granules, pellets, solutions, suspension, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.05% to 99% by weight of active ingredient(s) and at least one of (a) about 0.1% to 20% surfactant(s) and (b) about 1% to 99.95% solid or liquid diluent(s). More specifically, they will usually contain these ingredients in the following approximate proportions:

| | Percent by Weight | | |
|---|---|---|---|
| | Active Ingredient | Diluent(s) | Surfactant(s) |
| Wettable Powders | 5-90 | 1-94 | 1-10 |
| Oil Suspensions, Emulsions, Solutions (including Emulsifiable Concentrates) | 5-50 | 40-95 | 0-15 |
| Aqueous Suspensions | 5-50 | 40-94 | 1-20 |
| Dusts | 0.05-25 | 70-99.95 | 0-5 |
| Granules and Pellets | 0.05-95 | 1-99.95 | 0-15 |
| High Strength | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite, and synthetics. These synthetics can include precipitated, hydrated silicon dioxide; precipitated, hydrated calcium silicate; precipitated calcium carbonate and synthetic organics. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0°C. "McCutcheon's Detergents and Emulsifiers 1975 Annula". MC Publ. Corp., Ridgewood, N.J., as well as Sisely and Wood, "Encyclopedia of Surface Active Agents", Chemical Publ. Co., New York, 1964, list surfactants and recommended uses. All formulations can contain minor amounts of additives to reduce foam, caking, corrosion, microbiological growth, etc., or to mark visually the area that has been treated.

It is sometimes desirable to add ingredients to reduce the volatility of some of the compounds of this invention. Those additives can include film forming materials such as polyvinylpyrrolidones of molecular weights from about 20,000 to about 100,000; polyvinylalcohols of molecular weights from about 20,000 to about 150,000; and polyoxyethylenes of molecular weights from about 100,000 to about 6 × 10$^6$. These are a few examples of film forming additives. Any material which forms a film over solid active ingredient in the formulation preparation or a film over the active when sprayed and dried from a liquid formulation can be used. Other methods to reduce volatility may include the incorpotation of the compounds of this invention into resins, waxes, gums, rubbers, or the like, and then preparing formulations, as has been described above, for these combinations.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto preformed granular carriers. Suitable granular carriers include those suitable diluents listed earlier having a particle size range from USS Sieve No. 200 (74 microns) to USS Sieve No. 10 (2,000 microns). The preferred particle size range is from USS Sieve No. 140 (105 microns) to USS Sieve No. 20 (840 microns). Depending on the nature of the carrier, the active ingredient may remain on the surface of the carrier or be absorbed into the carrier. Usually, when the active ingredient remains on the surface of the carrier, a binding agent is used to hold the active ingredient on the surface. The binding agent should bind the active ingredient to the surface well enough so that no more than 10% of the active ingredient is removed during normal shipping and handling operations. Suitable binding agents include materials which are at least partially soluble in any liquid used in the manufacture of the granular formulation and which adhere to the granular surface. Water-soluble binders are preferred. Suitable binders include, but are not limited to, water-soluble polymers such as polyvinyl alcohol of molecular weights from about 20,000 to about 150,000; polyvinylpyrrolidones of molecular weights from about 20,000 to about 100,000 and polyoxyethylenes of molecular weights from about 100,000 to about $6 \times 10^6$. Other suitable binders include ligninsulfonates, starches, sugars, and certain surface active agents listed in "McCutcheon's Detergent and Emulsifiers 1975 Annual", MC Publ. Corp., Ridgewood, N.J.

The active ingredient may be sprayed onto preformed granular carriers as a solution in a suitable solvent, which may or may not be removed from the completed formulation. If the active ingredient is a liquid, it may be sprayed onto or mixed with the carrier directly. If it is a solid, it may be melted and applied directly as a liquid. If very low strength granules are desired, the active ingredient may be vaporized onto the carrier.

Granules may also be prepared by agglomeration techniques. For example, the active ingredient and a finely divided solid diluent may be mixed and agglomerated by techniques known in the art such as spraying with a liquid in a fluidized bed or pan granulator. The active ingredient and diluent may also be mixed with other formulation ingredients and pelletized. The pellets may then be crushed to a desired granular size. Pellets may be made by spraying the active material upon preformed granular carriers or by agglomeration techniques. See: J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for Example:

H. M. Loux, U.S. Pat. No. 3,235,361, Feb. 15, 1966, Col. 6, Line 16 through Col. 7, line 19 and Examples 10 through 41.

R. W. Luckenbaugh, U.S. Pat. No. 3,309,192, March 14, 1967, Col. 5 line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855 June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 5

Granule
  3-chloro-2-(phenyl)-4,5,6,7-tetrahydro- 2H-indazole — 10%
  attapulgite granules (low volatile matter, 0.71–0.30mm. U.S.S. #25–50 sieves) — 90%

The active ingredient is warmed to approximately 105° and sprayed upon dedusted and pre-warmed attapulgite granules in a double cone blender. The granules are then allowed to cool and are packaged.

EXAMPLE 6

Solution
  3-chloro-2-(phenyl)-4,5,6,7-tetrahydro-2H-indazole — 20%
  dimethylformamide — 80%

The ingredients are combined and stirred to produce a solution, which can be used for low-volume applications.

EXAMPLE 7

Extruded Pellet
  3-chloro-2-(phenyl)-4,5,6,7-tetrahydro-2H-indazole — 1%
  anhydrous sodium sulfate — 10%
  crude calcium ligninsulfonate — 5%
  sodium alkylnaphthalenesulfonate — 1%
  polyoxyethylene — 1%
  calcium/magnesium bentonite — 82%

The ingredients are blended, hammer milled and then moistened with about 12% water. The mixture is extruded as cylinders about 3mm. diameter which are cut to produce pellets about 3mm. long. These may be used directly after drying, or the dried pellets may be crushed to pass a U.S.S. No. 20 sieve (0.84mm., openings). The granules held on a U.S.S. No. 40 sieve (0.42mm. openings) may be packaged for use and the fines recycled. All compounds of this invention may be formulated in this manner.

EXAMPLE 8

Emulsifiable Concentrate
  3-chloro-2-(phenyl)-4,5,6,7-tetrahydro-2H-indazole — 20%
  blend of oil soluble sulfonates and polyoxyethylene ethers — 4%
  xylene — 76%

The ingredients are combined and stirred until solution is complete. A fine screen filter is included in packaging operation to insure the absence of any extraneous undissolved material in the product.

EXAMPLE 9

Aqueous Suspension
  3-chloro-2-(phenyl)-4,5,6,7-tetrahydro-2H-indazole — 40.0%
  polyacrylic acid thickner — 0.3%
  dodecylphenol polyethylene glycol ether — 0.5%
  disodium phosphate — 1.0% monosodium phosphate — 0.5%
polyvinyl alcohol — 1.0%
pentachlorophenol — 0.4%
water — 56.3%

The ingredients are ground together in a sand mill to produce particles essentially all under five microns in size.

EXAMPLE 10

Wettable Powder
   3-chloro-2-(phenyl)-4,5,6,7-tetrahydro-2H-indazole — 50%
   sodium alkylnaphthalenesulfonate — 2%
   sodium ligninsulfonate — 2%
   synthetic amorphous silica — 3%
   kaolinite — 43%

The ingredients are thoroughly blended, passed through an air mill to produce an average particle size under 15 microns, reblended, and sifted through a U.S.S. No. 50 sieve (0.3mm. opening) before packaging.

EXAMPLE 11

High Strength Concentrate
   3-chloro-2-(phenyl)-4,5,6,7-tetrahydro-2H-indazole — 99%
   trimethylnonyl polyethylene glycol ether — 1%

The surfactant is sprayed upon the actve ingredient in a blender and the mixture sifted through a U.S.S. No. 40 sieve (0.42mm. openings) prior to packaging. The concentrate may be formulated further for practical use.

EXAMPLE 12

Granule
   3-chloro-2-(phenyl)-4,5,6,7-tetrahydro-2H-indazole — 0.5%
   polyvinylpyrrolidone — 1%
   attapulgite granules (low volatile matter, 0.59–0.25 mm.; USS #30–60 mesh size) — 98.5%

Forty grams of a solution containing 2.5% 3-chloro-2-(phenyl)-4,5,6,7-tetrahydro-2H-indazole and 5% polyvinylpyrrolidone dissolved in methyl alcohol are slowly atomized onto a fluidized bed of attapulgite granules (197 gm.). Fluidization of the granules is continued after atomization is complete and until all the methyl alcohol is evaporated from the granules. The granules are packaged for use.

EXAMPLE 13

Extruded Pellet
   3-chloro-2-(phenyl)-4,5,6,7-tetrahydro-2H-indazole — 25%
   anhydrous sodium sulfate — 10%
   crude calcium ligninsulfonate — 5%
   sodium alkylnaphthalenesulfonate — 1%
   calcium/magnesium bentonite — 59%

The ingredients are blended, hammer milled and moistened with about 10–12% water. The mixture is then extruded as cylinders about 3mm. in diameter which are cut to be about 3mm. long. These pellets may be used directly after drying or the dried pellets may be crushed to pass a USS #20 sieve (0.84mm. opening). The pellets retained on a USS #40 sieve (0.42 mm. openings) may be packaged for use and the fines recycled.

EXAMPLE 14

Granule
   3-chloro-2-(phenyl)-4,5,6,7-tetrahydro-2H-indazole — 2%
   attapulgite granules (low volatile matter, 0.71–0.30 mm. USS #25–50 mesh sieves) — 98%

The active ingredient is warmed to approximately 105° and sprayed upon the dedusted and prewarmed granules in a double cone blender. The granules are allowed to cool and are packaged for use.

EXAMPLE 15

3-chloro-2-(phenyl)-4,5,6,7-tetrahydro-2H-indazole — 0.21%
Anhydrous sodium sulfate — 10%
Crude calcium ligninsulfonate — 5%
Sodium alkylnaphthalenesulfonate — 1%
Finely divided attapulgite clay — 83.8%

The ingredients are blended, hammer milled, and placed in a fluidized bed granulator. Water is aspirated into the fluidized bed of powder until small granules are formed. Water aspiration is then stopped, but fluidization is continued to dry the formed granules. The granules are removed from the granulator and screened to pass a USS Sieve No. 20 (0.42 mm. openings). Granules retained on a USS Sieve No. 40 (0.42 mm) openings are packaged for use. Granules larger than 0.84 mm. are ground and recycled. Fines smaller than 0.42 mm. are also recycled.

EXAMPLE 16

Extruded Pellet
   3-chloro-2-(phenyl)-4,5,6,7-tetrahydro-2H-indazole — 0.1%
   Anhydrous sodium sulfate — 10%
   Crude calcium ligninsulfonate — 5%
   Sodium alkylnaphthalenesulfonate — 1%
   Polyoxyethylene — 1%
   Calcium/magnesium bentonite — 82.9%

The ingredients are blended, hammer milled and then moistened with about 12% water. The moist mixture is extruded as cylinders about 1mm. diameter and 2mm. long. These small pellets are dried and packaged. They are applied directly.

EXAMPLE 17

Granule
   3-chloro-2-(phenyl)-4,5,6,7-tetrahydro-2H-indazole — 0.05%
   dimethylformamide — 5% s
   Attapulgite granules (low volatile matter, 0.59–0.25 mm. USS Sieve No. 30–60) — 94.95%

The active ingredient is dissolved in dimethylformamide. This solution is very slowly atomized onto a rapidly tumbling bed of the attapulgite granules. After application of the active ingredient is complete, the formulation is blended for a few additional minutes. The dimethylformamide is not removed from the formulation. The granules are packaged for use.

EXAMPLE 18

Emulsifiable Concentrate
   3-chloro-2-(phenyl)-4,5,6,7-tetrahydro-2H-indazole — 20%
   Blend of oil-soluble sulfonate with polyoxyethylene ethers — 6%
   Aromatic hydrocarbon solvent with a closed cup flash point between 100° and 115° F. — 74%

The ingredients are combined and stirred until solution is complete. The solution is filtered prior to packaging through a fine screen filter to remove any extraneous undissolved material.

EXAMPLE 19

Granule

Five grams of the emulsifiable concentrate of Example 18 is slowly atomized and sprayed onto attapulgite granules as described in Example 17. The solvent is now removed from the formulation, and the product is packaged for use.

EXAMPLE 20

Granule 3-chloro-2-(phenyl)-4,5,6,7-tetrahydro-2H-indazole — 0.1% sodium ligninsulfonate — 5%

Preformed sand granules having a particle size distribution from USS Sieve No. 140 (105 microns) to USS Sieve No. 50 (297 microns) — 94.9%

The active ingredient is dissolved in methyl alcohol and sodium ligninsulfonate is added. This mixture is slowly sprayed onto a tumbling bed of the sand granules. After spraying is complete, the tumbling granules are warmed to remove the methyl alcohol. The resulting granules are packaged for use.

Compositions can contain, in addition to the active ingredients of this invention, other conventional agricultural chemicals such as fertilizers, plant growth modifiers or herbicides.

For example, the compounds of Formula I can be combined with the following herbicides:

(1) 5-tert-butyl-3-(2,4-dichloro-5-isopropoxyphenyl)-1,3,4-oxadiazol-2-one;
(2) 6-methylthio-2,4-bis(ethylamino)-s-triazine;
(3) 3-isopropyl-(1H)-benzo-2,1,3-thiodiazin-4-one-2,2-dioxide;
(4) 2,4-dichlorophenoxyacetic acid and related esters and salts, Combination with wheat herbicides:

(1) 2,4-dichlorophenoxyacetic acid and related esters and salts:
(2) S-(2,2,3-trichloroallyl)-diisopropylthiocarbamate;
(3) Methyl 2-[4-(2,4-dichlorophenoxy(phenoxy)]-propanoate;
(4) 1,2-dimethyl-3,5-diphenyl-1H-pyrazolium methyl sulfate;
(5) 4-chloro-2-butynyl 3-chlorocarbanilate.

The compounds of Formula I can also be combined with other herbicides and are particularly useful in combination with bromacil [3-(sec-butyl)-5-bromo-6-methyluracil], diuron [3-(3,4-dichlorophenyl)-1,1-dimethylurea], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido) phenyl tert-butylcarbamate, 2-methyl-4-chlorophenoxyacetic acid, its salts or esters, 4-amino-6-tert-butyl-3-methylthio-as-triazin-5(4H)-one, aryl 4-nitrophenyl ethers such as 2,4,6-trichlorophenyl 4-nitrophenyl ether and 2,4-dichlorophenyl 4-nitrophenyl ether for controlling a broad spectrum of weeds.

The agriculatural chemicals listed above are exemplary of the compounds which can be mixed with the active compounds and are not intended to limit the invention in any way.

EXAMPLE 21

For industrial use, a granule may be made from 3-chloro-2-(phenyl)-4,5,6,7-tetrahydro-2H-indazole — 5%

3-cyclohexyl-1-methyl-6-dimethylamino-s-triazine-2,4(1H,3H)-dione — 5%

25-50 attapulgite granules — 90%

The active ingredients are mixed and then warmed to approximately 100° and sprayed onto the dedusted and prewarmed granules in a double cone blender. The treated granules are then allowed to cool and are packaged.

Utility

The compounds of formula I are useful for the selective preemergence control of undesired vegetation, e.g., barnyardgrass, in crops such as rice, in particular paddy rice, wheat and peanuts. These compounds also have utility for the postemergence control of weeds in certain crops, for example, rice. Furthermore, compounds of this invention can be used as directed treatments for the pre- or post-emergence control of weeds in various crops including soybeans, peanuts, cotton, garden beans and row-planted rice.

The compounds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may also be applied after the crop is transplanted if care is taken to keep the chemical off the crop foliage.

The precise amount of the compounds of Formula I to be used in any given situation will vary according to the particular end result desired, the use involved, the crop and weed species, and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.1 to about 30 kilograms per hectare, preferably about 0.5 to about 15 kilograms per hectare. The lower rates in this range will generally be selected on lighter soils, soils low in organic matter content, for selective weed control in crops, or in situations where maximum persistance is not necessary.

Herbicidal activity of compounds of this invention was discovered in greenhouse tests, as explained below:

Procedure Test 1

Seeds of crabgrass (*Digitaria* spp.), barnyardgrass (*Echinochloa crusgalli*), wild oats (*Avena fatua*), Cassia tora, morningglory (*Ipomoea* sp.), cocklebur (*Xanthium* sp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

Ratings for compounds tested by this procedure are recorded in Table 1. Plant response in all tables is expressed on a scale extending from 0 = no injury to 10 = complete kill. Letter symbols used had the following meanings: B = burn, G = growth retardation, C = necrosis/chlorosis, E = emergence inhibition, and H = formative effect.

TABLE 1

| Compound | Kg/Ha | Bush bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| POST EMERGENCE | | | | | | | | | | | | | | | |
| 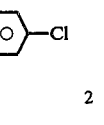 | 2/5 | 9B | 7B | 10B | 2B | 1B | 1B | 2B | 6B | 3B | 3B | 2B | 1B | — | 5B |
| 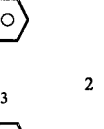 | 2 | 5B | 4B | 1B | 1B | 3B | 0 | 5B | 0 | 0 | 2B | 1B | 0 | 0 | 3B |
| 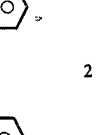 | 2 | 2B | 4B | 5B | 0 | 0 | 0 | 1B | 3B | 0 | 0 | 0 | 1B | 0 | 1B |
| 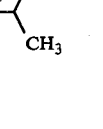 | 2 | 8B | 7B | 7B | 2B | 2B | 1B | 6B | 7B | 1B | 1B | 4B | 5B | 2B | 8B |

| Compound | Kg/Ha | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| PRE-EMERGENCE | | | | | | | | | | | | | |
| 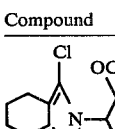 | 2/5 | 0 | 0 | 0 | 0 | 0 | 2C 8H | 2C | 1C | 3C 8H | 1H | 0 | 2C |
| 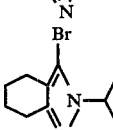 | 2 | 0 | 0 | 10E | 0 | 3G | 2C | 0 | 1C | 3H | 0 | 0 | 1C |
| 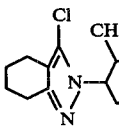 | 2 | 2G | 0 | 0 | 0 | 0 | 0 | 0 | 0 | 0 | 0 | 0 | 0 |
| 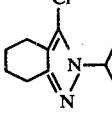 | 2 | 0 | 0 | 0 | 5G | 5G | 5G | 0 | 0 | 0 | 0 | 0 | 0 |

| Compound | Kg/Ha | Bush bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| POST EMERGENCE | | | | | | | | | | | | | | | |
| 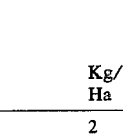 | 2 | 8B | 3B | 9B | 3B | 1B | 1B | 3B | 10B | 3B | 2B | 6B | 5B | 5B | 9B | and

TABLE 1-continued

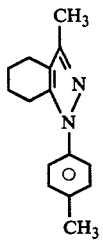

| Compound | Kg/Ha | PRE-EMERGENCE | | | | | | | | | | | |
|---|---|---|---|---|---|---|---|---|---|---|---|---|---|
| | | Morning Glory | Cocklebur | Cassia | Nutsedge | Crabgrass | Barnyard-Grass | Wild Oats | Wheat | Corn | Soybean | Rice | Sorghum |
| 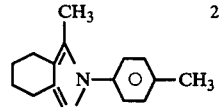 and 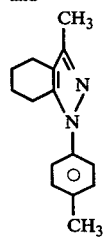 | 2 | 0 | 10E | 1C | 0 | 6C | 6C | 0 | 0 | 6C | 6G | 0 | 1C |

| Compound | Kg/Ha | POST EMERGENCE | | | | | | | | | | | | |
|---|---|---|---|---|---|---|---|---|---|---|---|---|---|---|
| | | Bush bean | Cotton | Morning Glory | Cocklebur | Cassia | Nutsedge | Crabgrass | Barnyard Grass | Wild Oats | Wheat | Corn | Soybean | Rice | Sorghum |
| 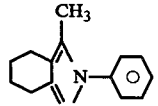 | 2 | 7B | 6B | 4B | 1B | 1B | 0 | 4B | 7B | 2B | 1B | 4B | 3B | 3B | 4B |
| 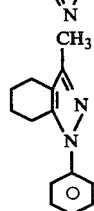 | | | | | | | | | | | | | | | |
| 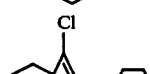 | 2 | 9B | 3B | 10B | 2B | 1B | 1B | 6B | 9B | 2B | 3B | 7B | 5B | 3B | 10B |
| 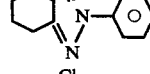 | 2/5 | 5B | 6B | 6B | 4B | 1B | 1B | 1B 2H | 6B | 1B | 1B | 4B | 4B | 2B | 2B |

| Compound | Kg/Ha | PRE-EMERGENCE | | | | | | | | | | | |
|---|---|---|---|---|---|---|---|---|---|---|---|---|---|
| | | Morning Glory | Cocklebur | Cassia | Nutsedge | Crabgrass | Barnyard-Grass | Wild Oats | Wheat | Corn | Soybean | Rice | Sorghum |
| 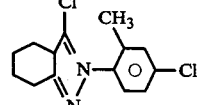 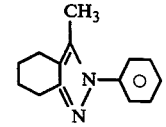 | 2 | 0 | 0 | 0 | 0 | 1C | 8C | 0 | 0 | 4G | 0 | 0 | 0 |

TABLE 1-continued

| Compound | Rate | | | | | | | | | | | | |
|---|---|---|---|---|---|---|---|---|---|---|---|---|---|
| [4-methyl-1-phenyl-4,5,6,7-tetrahydro-1H-indazole with Cl] | 2 | 1C | 0 | 0 | 0 | 5G | 8C | 2C | 2C | 2C | 2G | 2C | 2C |
| [4-chloro-1-(4-chloro-2-methylphenyl)-... tetrahydroindazole] | 2/5 | 0 | 0 | 0 | 0 | 0 | 5C | 1C | 0 | 1H | 0 | 1C | 3G |

Table 2, is presented to further illustrate the biological activity of the compounds of this invention. The data illustrates the herbicidal efficacy of the compounds with selectively for two important crops, ric and wheat. were maintained in a greenhouse (glasshouse), and visual plant response ratings (as described in Table 1) were generally taken about three weeks after application.

TABLE 2

| COMPOUND | Rate kg ai/ha | Intermediate Rice | Japonica Rice | Barnyard-grass | Morning-glory | Wheat | Wild Oats | Bromus tectorum | Bromus secalinus |
|---|---|---|---|---|---|---|---|---|---|
| [Cl, CH₃O-substituted compound] | 1/8 | 0 | — | 7C | 0 | — | — | — | — |
|  | 1/2 | 0 | 0 | 3G | 0 | — | — | — | — |
| [Br-substituted phenyl compound] | 2 | 0 | 0 | 0 | 0 | 0 | 0 | 0 | 0 |
|  | 4 | 0 | 0 | 6C | 0 | 0 | 0 | 4C | 0 |
|  | 8 | 0 | 0 | 10C | 0 | 0 | 8C | 9C | 4C |
| [Cl, CH₃-substituted compound] | 4 | 0 | 0 | 5C | 0 | 0 | 0 | 2C | 0 |
|  | 8 | — | — | — | — | 0 | 0 | 9C | 0 |
| [CH₃-substituted compound (mixture "and")] | 2 | 0 | 0 | 0 | 0 | 0 | 0 | 0 | 0 |
|  | 4 | — | 0 | 1C | 0 | 0 | 0 | 0 | 0 |
|  | 8 | 0 | 0 | 8C | 0 | 0 | 1C | 9C | 8C |
| [Cl-substituted phenyl compound] | 2 | 0 | 0 | 1C | 0 | 0 | 0 | 0 | 0 |
|  | 4 | 0 | 0 | 7C | 0 | 2C | 0 | 8C | 0 |
|  | 8 | 0 | 0 | 9C | 0 | 2C | 6C | 8C | 4C |
| [Cl-substituted, 2-methylphenyl compound] | 16 | 0 | 0 | 9C | 0 | 0 | 0 | 0 | 9C |

The test compounds were applied in a non-phytotoxic solvent to soil pots containing seeds of an intermediate hybrid rice, japonica rice, barnyardgrass (*Echinochloa crusgalli*), morning glory (*Ipomoea* sp.), wheat, wild oats (*Avena fatua*), downy brome (*Bromus tectorum*), and cheat (*Bromus secalinus*). The plants It should be noted that, in general, these compounds at a low concentration virtually eliminated the undesirable vegetation, e.g., barnyardgrass, but had relatively little effect on the crops, e.g., rice. In wheat, cheat and downy brome, were often controlled with little or no effect on the wheat crop.

The following table, Table 3, is presented to additionally illustrate the biological activity of the compounds of the present invention. The data illustrate the herbicidal efficacy of the compounds with selectivity for the rice in paddy culture.

A rice paddy was constructed using a tub containing soil and barnyardgrass (*Echinochloa crusgalli*) seeds, and japonica rice plants which were transplanted into the paddy soil when in the two to three-leaf stage. The water level was maintained a few centimeters above the soil surface. Test samples were applied directly into the paddy water, and plant response raings were taken three weeks later.

TABLE 3

| COMPOUND | Rate kg ai/ha | Japonica Rice | Barnyardgrass |
|---|---|---|---|
| 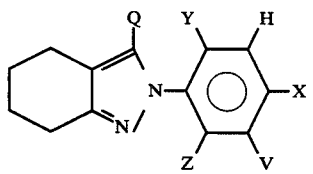 | 1/2 | 0 | 2G |
| | 1 | 0 | 9G |
| | 2 | 0 | 9G |
| | 4 | 0 | 9C |

I claim:

1. A compound of the formula:

$$\text{(I)}$$

where
Q is chlorine, bromine or methyl;
X is hydrogen or methyl;
Y is hydrogen or methyl;
V is hydrogen or methyl; and
Z is hydrogen or methyl; with the proviso that at least one of X, Y, V or Z must be hydrogen.

2. A compound of claim 1 wherein Q is chlorine or methyl.

3. A compound of claim 1 wherein X, Y, Z or V are hydrogen or methyl and Q is chlorine or methyl.

4. The compound of claim 1, 3-chloro-2-(phenyl)-4,5,6,7-tetrahydro-2H-indazole.

5. The compound of claim 1, 2-(phenyl)-3-methyl-4,5,6,7-tetrahydro-2H-indazole.

6. A composition for the control of undesirable vegetation consisting essentially of a herbicidally effective amount of a compound of claim 1 and at least one of (a) a surface-active agent and (b) a solid or liquid diluent.

7. A compound for the control of undesirable vegetation consisting essentially of a compound of claim 2 and at least one of (a) a surface-active agent and (b) a solid or liquid diluent.

8. A composition for the control of undesirable vegetation consisting essentially of a herbicidally effective amount of a compound of claim 3 and at least one of (a) a surface-active agent and (b) a solid or liquid diluent.

9. A composition for the control of undesirable vegetation consisting essentially of a herbicidally effective amount of the compound of claim 4 and at least one of (a) a surface-active agent and (b) a solid or liquid diluent.

10. A composition for the control of undesirable vegetation consisting essentially of a herbicidally effective amount of the compound of claim 5 and at least one of (a) a surface-active agent and (b) a solid or liquid diluent.

11. A method for the control of undesirable vegetation comprising applying to the locus of such undesirable vegetation a herbicidally-effective amount of a compound of claim 1.

12. A method for the control of undesirable vegetation comprising appluying to the locus of such undesirable vegetation a herbicidally-effective amount of a compound of claim 2.

13. A method for the control of undesirable vegetation comprising applying to the locus of such undesirable vegetation a herbicidally-effective amount of a compound of claim 3.

14. A method for the control of undesirable vegetation comprising applying to the locus of such undesirable vegetation a herbicidally-effective amount of the compound of claim 4.

15. A method for the control of undesirable vegetation comprising applying to the locus of such undesirable vegetation a herbicidally-effective amount of the compound of claim 5.

16. A method for the control of barnyardgrass in rice comprising applying to the locus of such barnyardgrass a herbicidally-effective amount of a compound of claim 1.

17. A method for the control of barnyardgrass in rice comprising applying to the locus of such barnyardgrass a herbicidally-effective amount of a compound of claim 2.

18. A method for the control of barnyardgrass in rice comprising applying to the locus of such barnyardgrass a herbicidally-effective amount of a compound of claim 3.

19. A method for the control of barnyardgrass in rice comprising applying to the locus of such barnyardgrass a herbicidally-effective amount of the compoound of claim 4.

20. A method for the control of barnyardgrass in rice comprising applying to the locus of such barnyardgrass a herbicidally-effective amount of the compound of claim 5.

21. A method for the control of undesirable vegetation in wheat comprising applying to the locus of such undesirable vegetation a herbicidally-effective amount of a compound of claim 1.

22. A method for the control of undesirable vegetation in wheat comprising applying to the locus of such undesirable vegetation a herbicidally-effective amount of the compound of claim 4.

23. A method for the control of undesirable vegetation in paddy rice comprising applying to the locus of such undesirable vegetation a herbicidally-effective amount of a compound of claim 1.

24. A method for the control of undesirable vegetation in paddy rice comprising applying to the locus of such undesirable vegetation a herbicidally-effective amount of the compound of claim 4.

25. A method for the control of undesirable vegetation in transplanted crops which comprises applying to the locus of such undesirable vegetation a herbicidally-effective amount of a compound of claim 1.

26. A method for the control of undesirable vegetation in transplanted crops comprising applying to the locus of such undesirable vegetation a herbicidally-effective amount of the compound of claim 4.

* * * * *